(12) United States Patent
Stark

(10) Patent No.: US 6,342,698 B1
(45) Date of Patent: Jan. 29, 2002

(54) METHOD FOR CALIBRATING PHOTOMULTIPLIER TUBES IN A SCINTILLATION CAMERA

(75) Inventor: Iain Stark, Nepean (CA)

(73) Assignee: IS² Research Inc., Ontario (CA)

( * ) Notice: Subject to any disclaimer, the term of this patent is extended or adjusted under 35 U.S.C. 154(b) by 0 days.

(21) Appl. No.: 09/127,990

(22) Filed: Aug. 3, 1998

(30) Foreign Application Priority Data

Aug. 1, 1997 (CA) ............................................. 2212196

(51) Int. Cl.⁷ ............................................. G01T 1/208
(52) U.S. Cl. ................. 250/363.09; 250/252.1
(58) Field of Search .................. 250/363.09, 252.1 A, 250/207, 369, 363.07

(56) References Cited

U.S. PATENT DOCUMENTS

| | | |
|---|---|---|
| 3,900,731 A | 8/1975 | Chevalier et al. |
| 4,047,034 A | 9/1977 | Auphan |
| 4,079,257 A | 3/1978 | Jatteau et al. |
| 4,272,677 A | 6/1981 | Berthold et al. |
| 4,516,025 A | 5/1985 | Yamakawa et al. |
| 4,517,460 A | 5/1985 | Meulenbrugge et al. |
| 4,583,187 A | 4/1986 | Stoub |
| 4,605,856 A | 8/1986 | Persyk et al. |
| 4,611,117 A | 9/1986 | Seibert et al. |
| 4,882,495 A | 11/1989 | Tanaka |
| 5,004,904 A | 4/1991 | Yamakawa et al. |
| 5,237,173 A | 8/1993 | Stark et al. |
| 5,373,161 A | * 12/1994 | Tararine et al. ........ 250/363.09 |

FOREIGN PATENT DOCUMENTS

| | | |
|---|---|---|
| EP | 0 066 763 A1 | 12/1982 |
| EP | 0 450 388 B1 | 10/1991 |

* cited by examiner

Primary Examiner—Georgia Epps
Assistant Examiner—Richard Hanig
(74) Attorney, Agent, or Firm—Finnegan, Henderson, Farabow, Garrett & Dunner, L.L.P.

(57) ABSTRACT

A method for calibrating photomultiplier tubes in a scintillation camera having a plurality of light sources includes the steps of: pulsing all light sources simultaneously; reading the output of each photomultiplier tube; comparing the output of each photomultiplier tube with an expected value; determining whether the output of each photomultiplier tube is within a first specified tolerance; and adjusting each photomultiplier tube if the output of the photomultiplier tube is not within the first specified tolerance.

8 Claims, 15 Drawing Sheets

METHOD FOR CALIBRATING PHOTOMULTIPLIER TUBES IN A SCINTILLATION CAMERA

FIELD OF INVENTION

The present invention relates to a method for calibrating photomultiplier tubes in a scintillation camera having a plurality of light sources.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In order to operate a scintillation camera as described above, the patient should be supported horizontally on a patient support or stretcher.

The detector head of the scintillation camera must be able to pass underneath the patient. Therefore, in order for the scintillation camera to generate images from underneath the patient, the patient support must be thin. However, detector heads are generally supported by a pair of arms which extend from a gantry. Thus, the patient support generally must be cantilevered in order for the detector head to be able to pass underneath the patient without contacting any supporting structure associated with the patient support. The design of a cantilevered patient support that is thin enough to work properly with a scintillation camera is exceedingly difficult. Expensive materials and materials that are difficult to work with, such as carbon fibre, are often used in the design of such cantilevered patient supports.

A certain design of gantry or support structure for a scintillation camera includes a frame upon which a vertically oriented annular support rotates. Extending out from the rotating support is an elongate support. The elongate generally comprises a pair of arms. The pair of arms generally extends through a corresponding pair of apertures in the rotating support. One end of the pair of arms supports the detector head on one side of the annular support. The other end of the pair of arms supports a counter balance weight. Thus, the elongate support is counterbalanced with a counterweight on the opposite side of the detector head.

With such a design of support structure for a scintillation camera, a patient must lie on a horizontally oriented patient support. The patient support must be cantilevered so that the detector head can pass underneath the patient. If the detector head must pass underneath only one end of the patient, such as the patient's head, the cantilevered portion of the patient support is not long enough to cause serious difficulties in the design of the cantilevered patient support. However, if the camera must be able to pass under the entire length of the patient, the entire patient must be supported by the cantilevered portion of the patient support. As the cantilevered portion of the patient support must be thin so as not to interfere with the generation of images by the scintillation camera, serious design difficulties are encountered.

Among the advantages associated with such a design of support structure is that a patient may be partially passed through the orifice defined by the annular support so that the pair of arms need not be as long. However, the patient support must be able to support the patient in this position relative to the annular support, must be accurately positionable relative to the annular support, and must not interfere either with the rotation of the annular support or with the cable which will inevitably extend from the detector head to a nearby computer or other user control.

The photomultiplier tubes in a scintillation camera generate electric signals. The signals are processed, and images are created corresponding to the radiation emitted by the patient.

The photomultiplier tubes in a scintillation camera must be calibrated from time to time, that is, gain calibration must be performed, to ensure that their output remains constant.

Scintillation cameras generally include an light emitting diode for each photomultiplier tube. Typically, to calibrate the photomultiplier tube, the light emitting diode for that particular photomultiplier tube is pulsed, that is, is activated so as to provide a pulse of light. The output of the photomultiplier tube is compared with a known or expected value, such as a previously measured output of the photomultiplier tube.

If the output of the photomultiplier tube corresponds to the expected value, within a certain tolerance, the photomultiplier tube likely needs no calibration.

If the output of the photomultiplier tube is different from the expected value, that is, outside the tolerance, the photomultiplier tube is probably in need of calibration. However, it is possible that the photomultiplier tube does not need calibration, but rather that it is the output of the light emitting diode that has changed.

A prior art method of determining whether the output of the light emitting diode has changed is disclosed in U.S. Pat. No. 5,237,173 to Stark et al. In the disclosed method, the light emitting diode is pulsed. The output of the corresponding photomultiplier tube is then compared with the expected value. The output of the surrounding photomultiplier tubes are then compared with their expected values. If the outputs of all the photomultiplier tubes do not equal their expected values, within an appropriate tolerance, then it is likely that it is the light emitting diode that is malfunctioning. However, if it is only the output of the photomultiplier tube being calibrated that does not correspond to its expected value, then it is likely that it is the photomultiplier tube that is in need of calibration.

The above process is repeated for each photomultiplier tube. Accordingly, one disadvantage of this prior art method is that it is slow.

SUMMARY OF THE INVENTION

An object of the invention is to provide an improved an improved method for calibrating photomultiplier tubes in a scintillation camera.

The invention relates to a method and apparatus for calibrating photomultiplier tubes in a scintillation camera having a plurality of light sources. The method includes the steps of: pulsing all light sources simultaneously; reading the output of each photomultiplier tube; comparing the output of each photomultiplier tube with an expected value; determining whether the output of each photomultiplier tube is within a first specified tolerance; and adjusting each photomultiplier tube if the output of the photomultiplier tube is not within the first specified tolerance.

An embodiment of the invention also relates to a method and apparatus for calibrating photomultiplier tubes in a scintillation camera having a plurality of light sources. The method includes the steps of: pulsing all light sources simultaneously; reading the output of each photomultiplier tube; summing the outputs of the photomultiplier tubes; comparing the sum of the outputs of the photomultiplier tubes with an expected sum; determining whether the sum of the outputs of the photomultiplier tubes is within a second specified tolerance; adjusting the light sources if necessary, if the sum of the outputs of the photomultiplier tubes is not within the second specified tolerance, and repeating the above steps; comparing the output of each photomultiplier tube with an expected value; determining whether the output of each photomultiplier tube is within a first specified tolerance; adjusting each photomultiplier tube if the output of the photomultiplier tube is not within the first specified tolerance; comparing the output of each photomultiplier tube with the sum of the outputs of the photomultiplier tubes divided by the number of photomultiplier tubes; determining whether the output of each photomultiplier tube is within a third specified tolerance; and adjusting each photomultiplier tube if the photomultiplier tube is not within the third specified tolerance.

The invention also relates to a scintillation camera for obtaining a distribution image of incident gamma rays from a subject, the camera having a scintillator for emitting flashes of light due to incident gamma rays, a plurality of photomultiplier tubes optically coupled with said scintillator for converting the light flashes into respective electric signals which are individually detectable. The scintillation camera includes: a plurality of pulsible light sources, the plurality of light sources being simultaneously pulsible; pulsing means for pulsing the light sources simultaneously; and gain calibration means for comparing an output of each photomultiplier tube to an expected value, and carrying out an effective gain adjustment for each photomultiplier tube.

Other advantages, objects and features of the present invention will be readily apparent to those skilled in the art from a review of the following detailed description of preferred embodiments in conjunction with the accompanying drawings and claims.

BRIEF DESCRIPTION OF THE DRAWINGS

The embodiments of the invention will now be described with reference to the accompanying drawings, in which.

Figure 1:
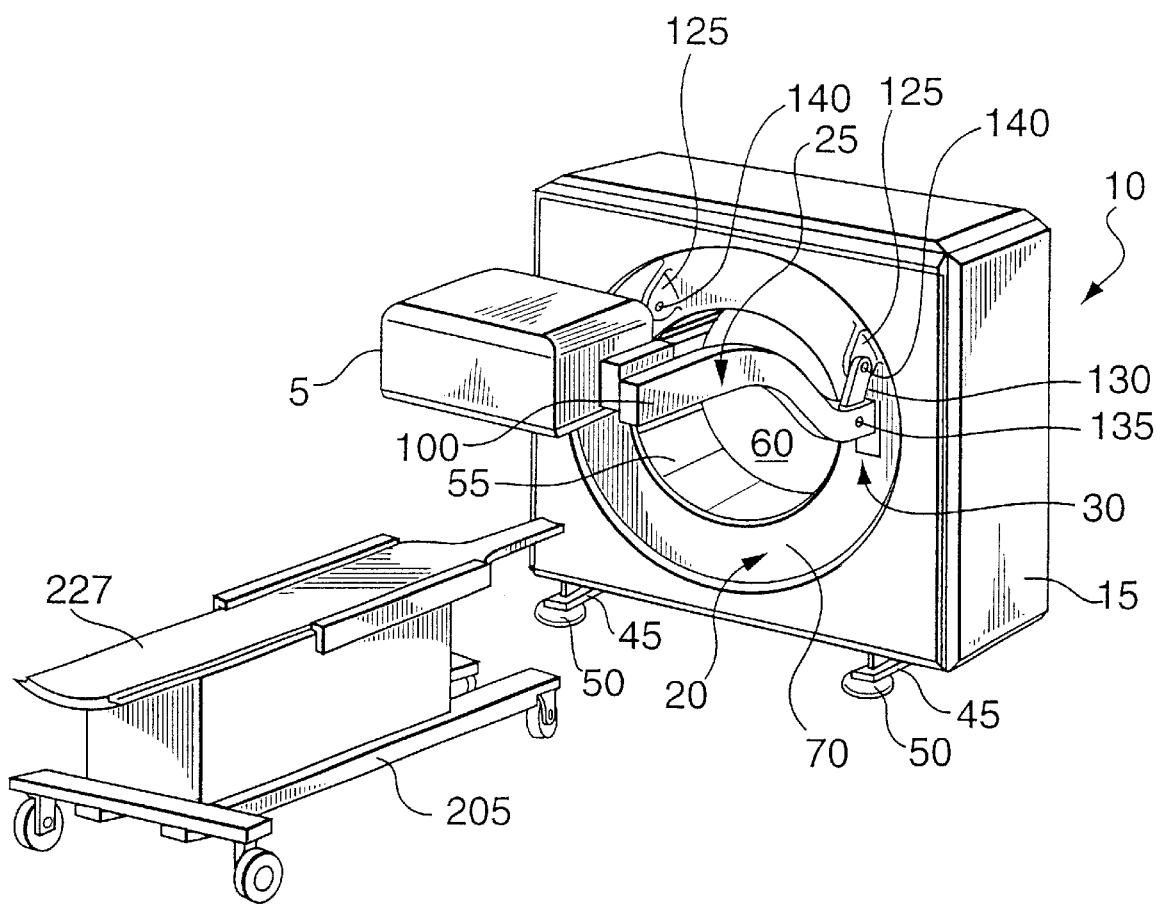
FIG. 1 is a perspective view of a scintillation camera including a detached patient support in accordance with the invention.
Figure 2:
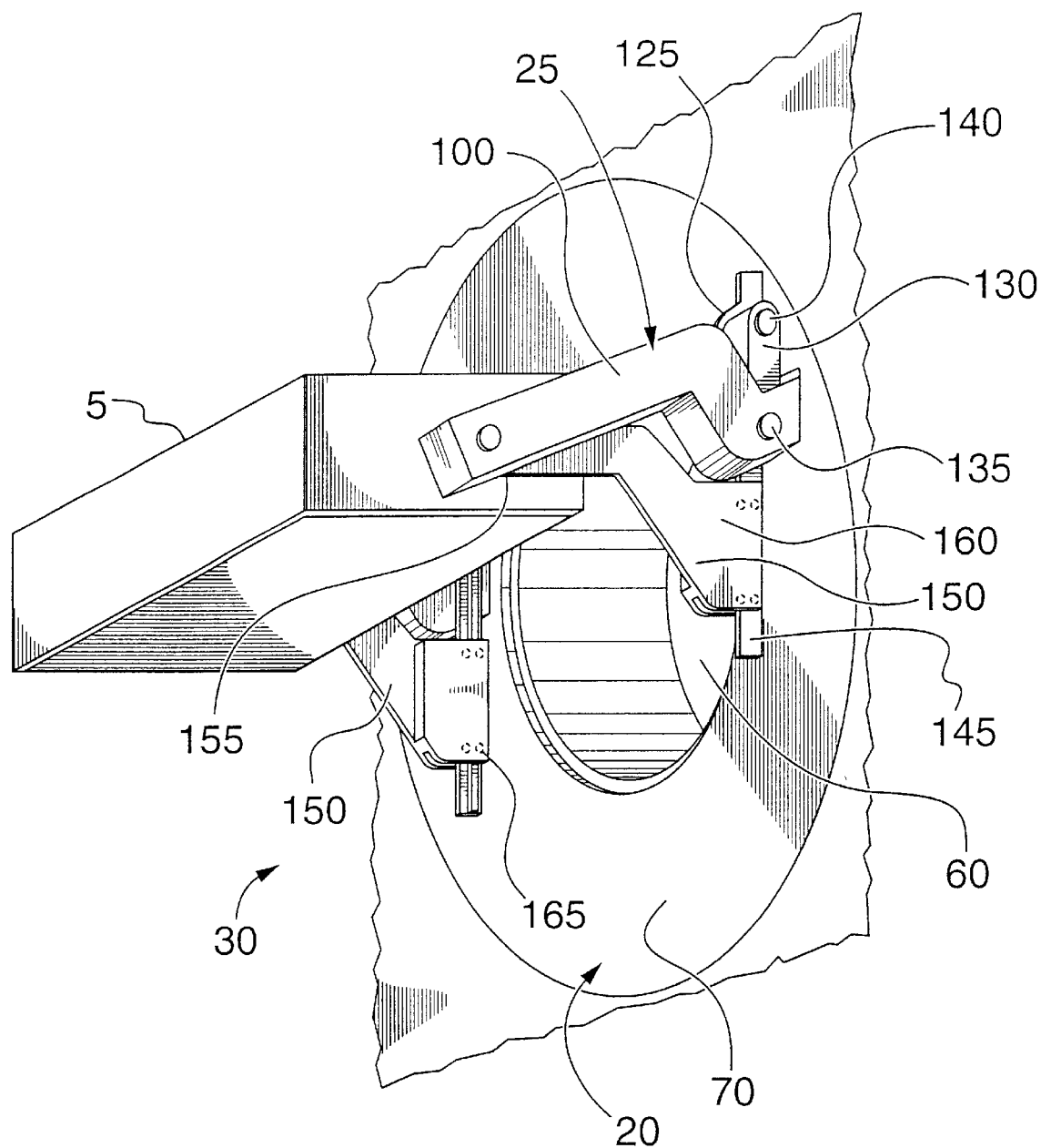
FIG. 2 is a perspective view of the guide of a scintillation camera.
Figure 3:
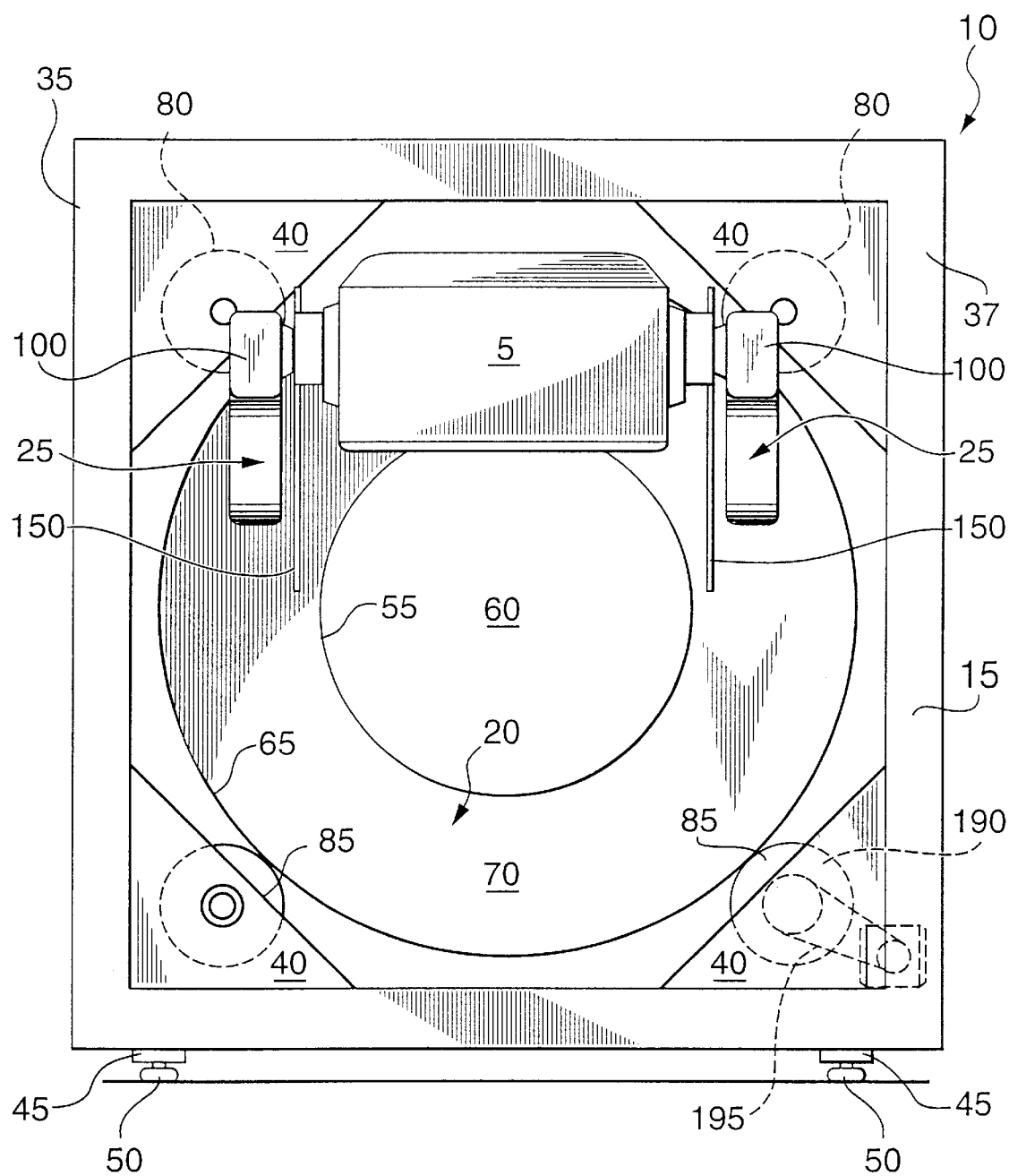
FIG. 3 is a front elevation view of a scintillation camera.
Figure 4:
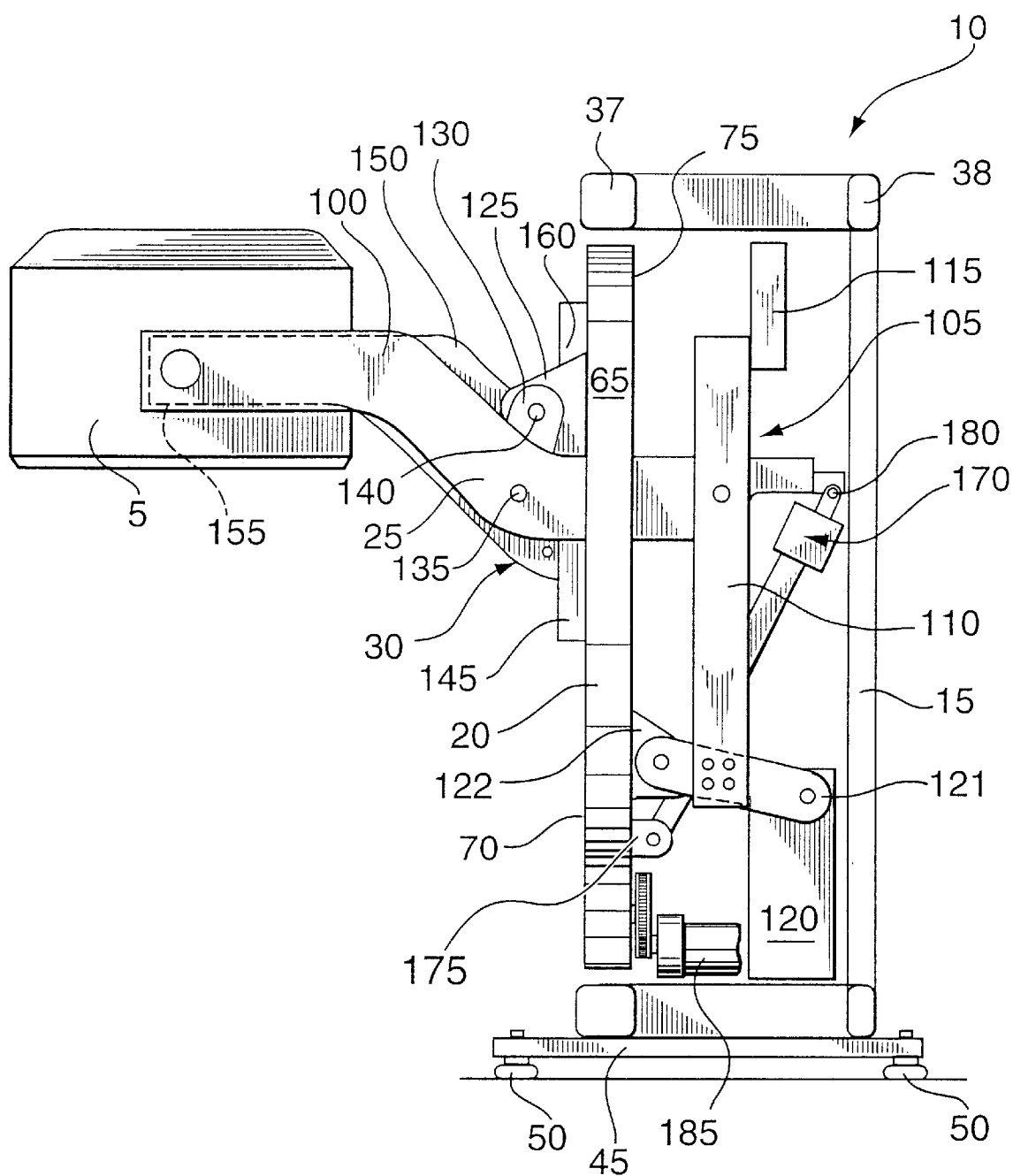
FIG. 4 is a side elevation view of a scintillation camera.
Figure 5:
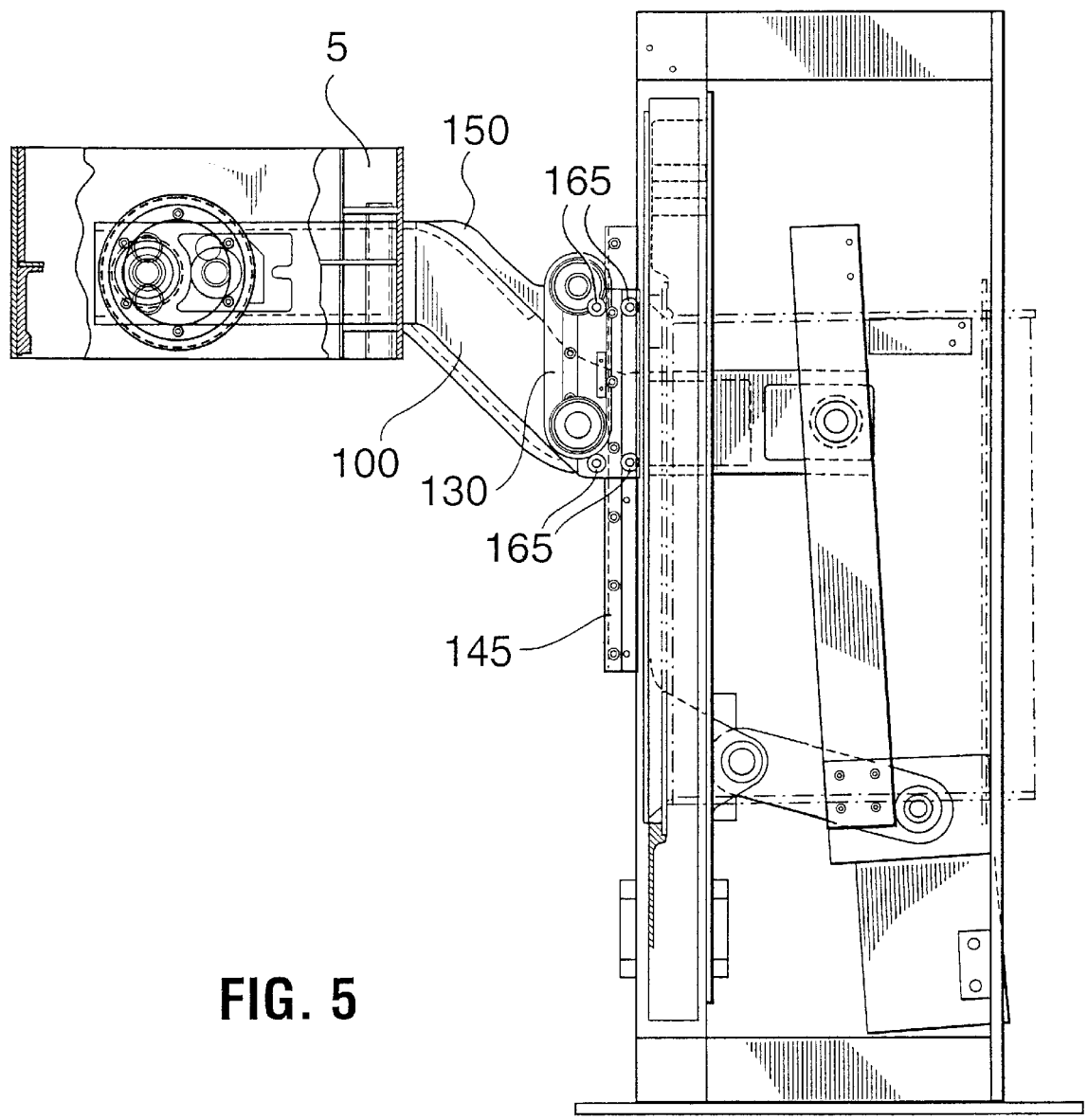
FIG. 5 is a side elevation view of a scintillation camera.
Figure 6:
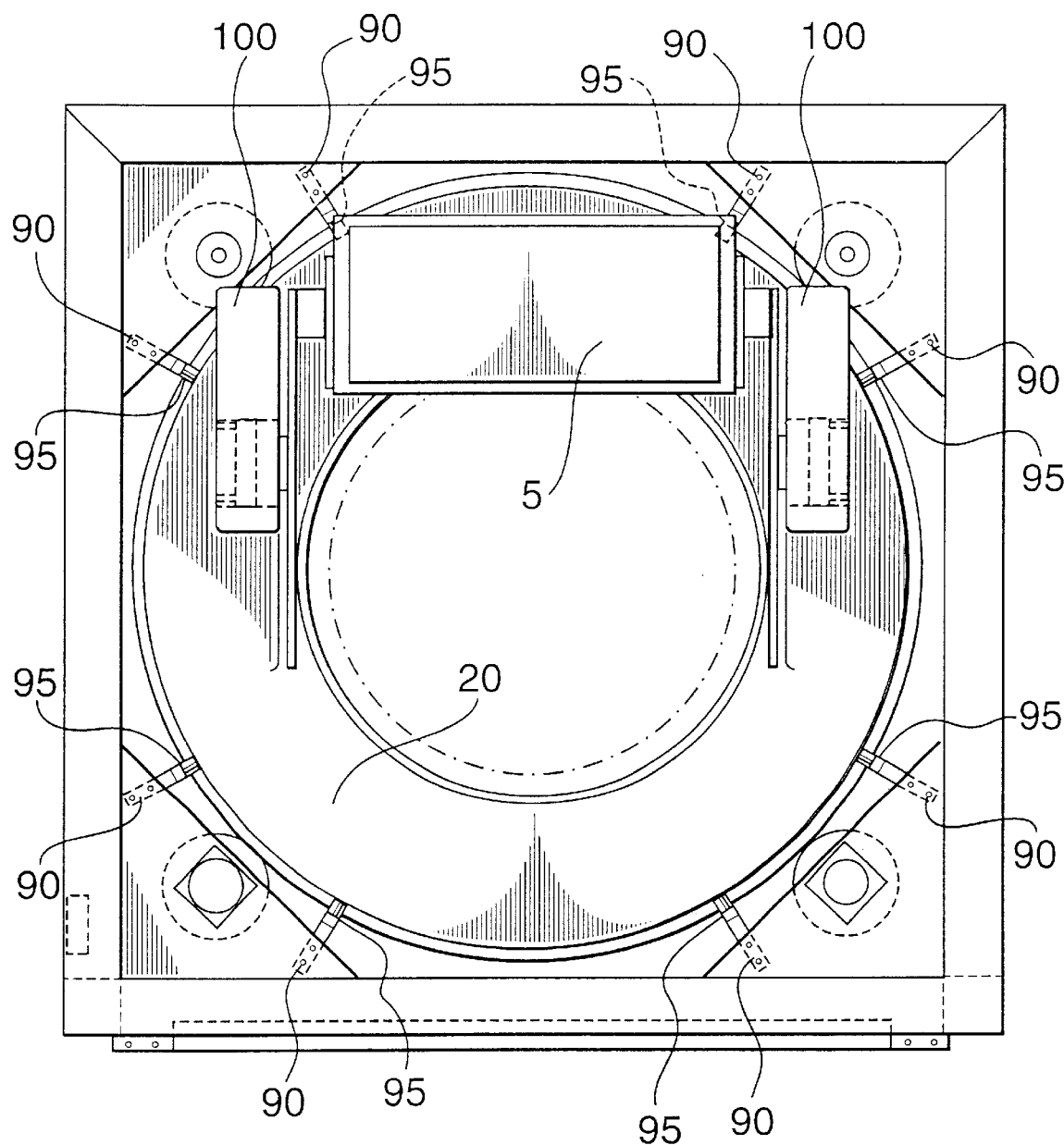
FIG. 6 is a front elevation view of a scintillation camera.
Figure 7:
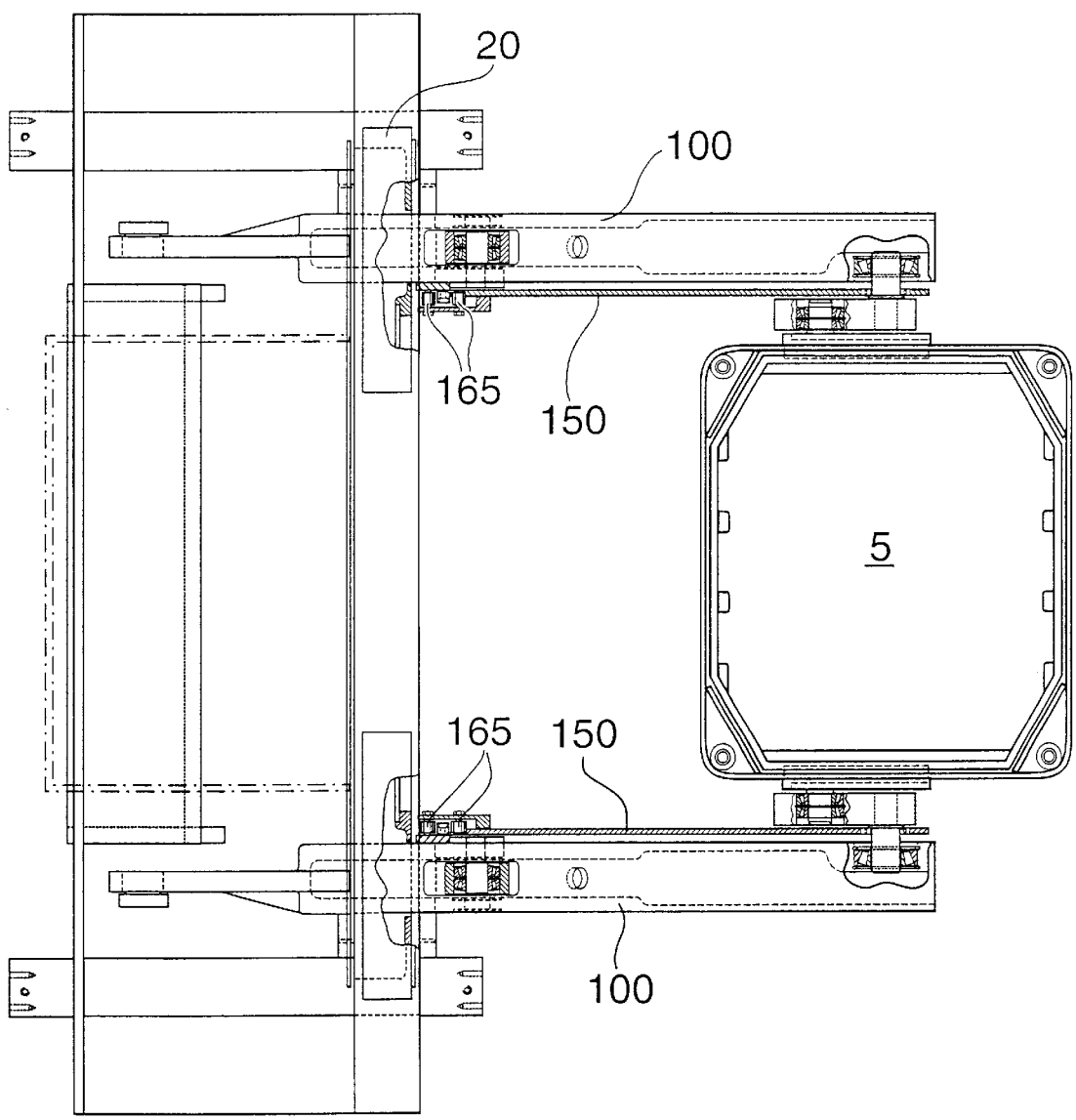
FIG. 7 is a top plan view of a scintillation camera.
Figure 8:
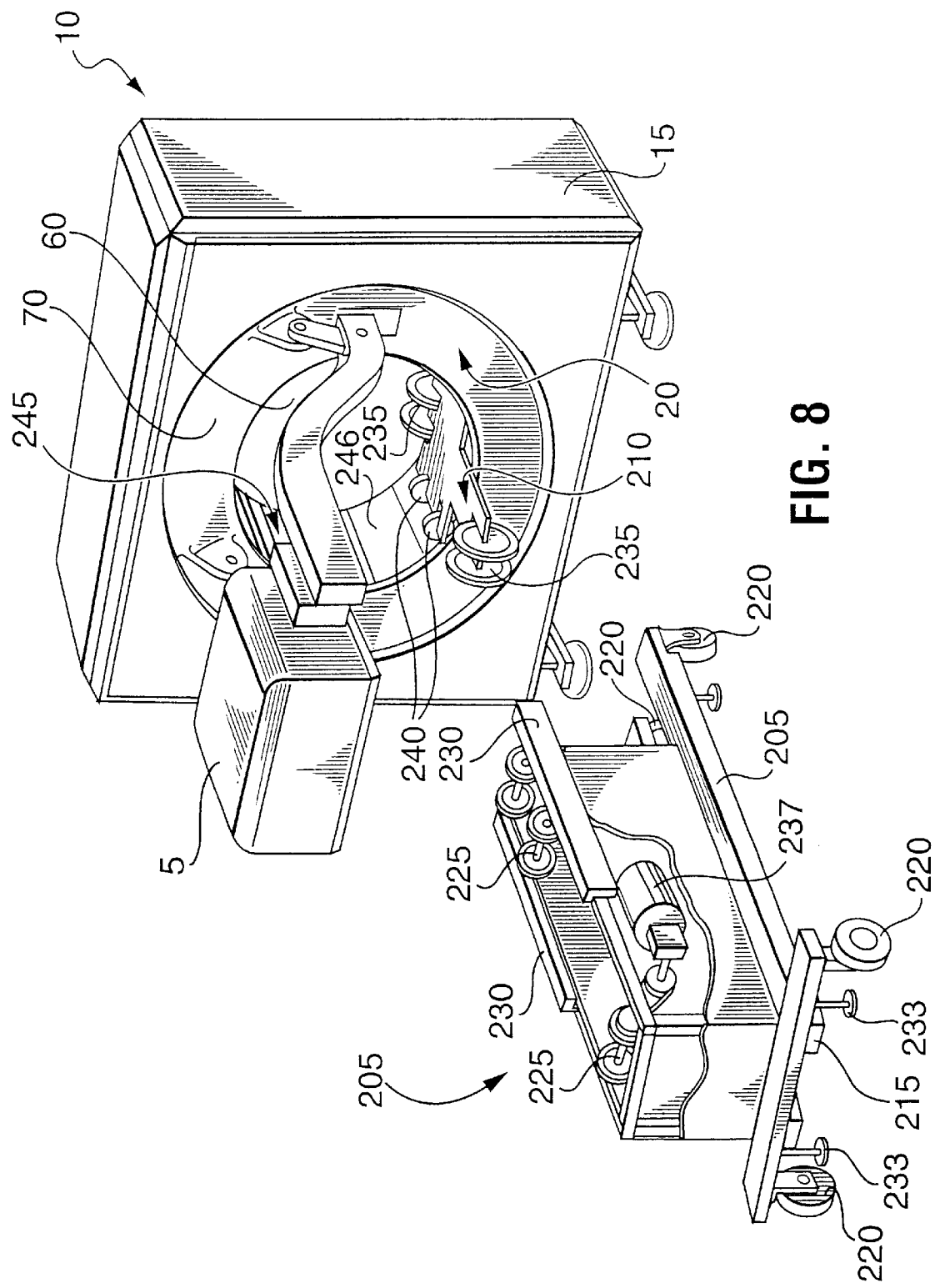
FIG. 8 is a perspective view of the scintillation camera of FIG. 1, including the detached patient support and engaged patient support, with the stretcher removed.
Figure 9:
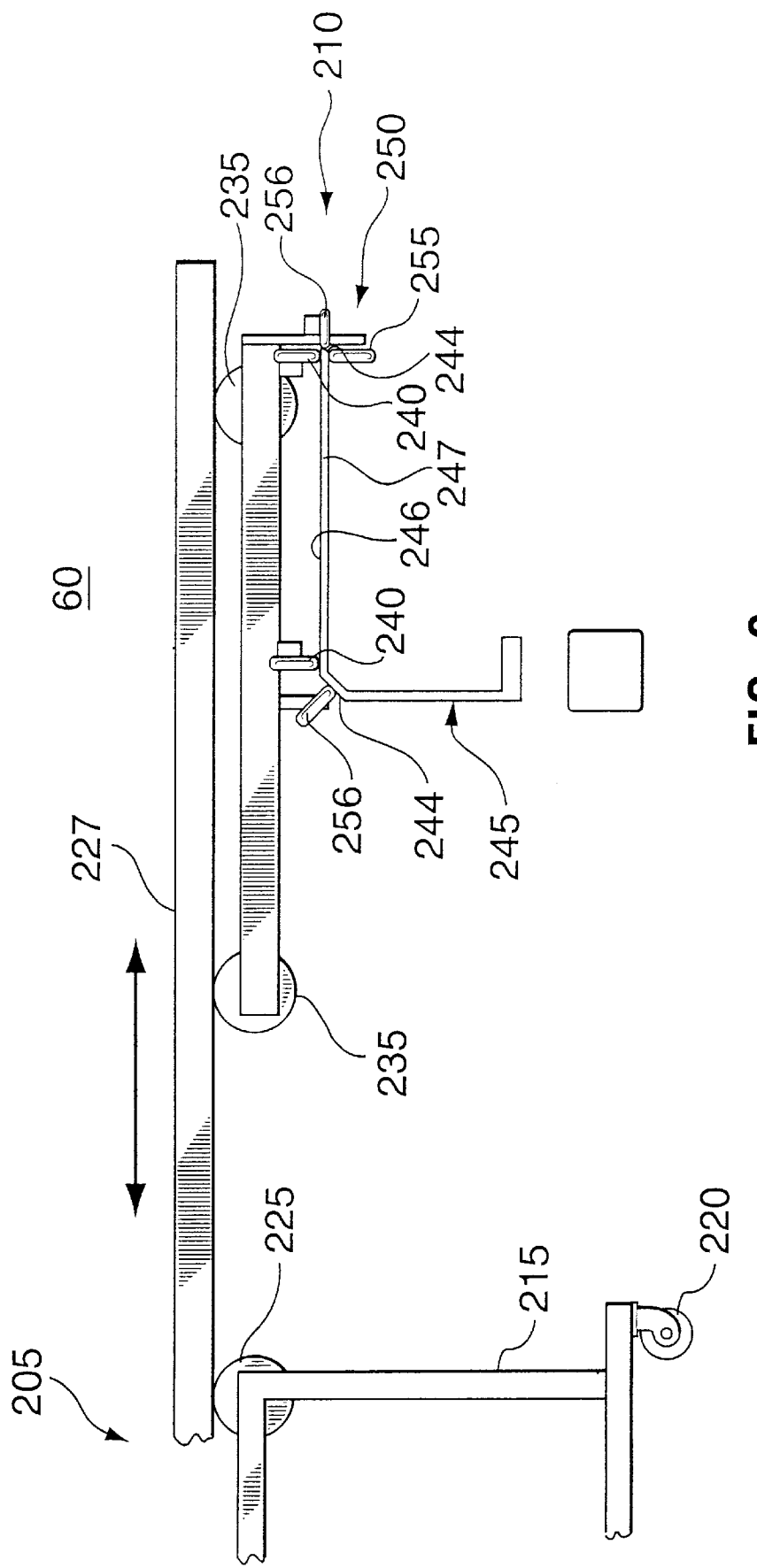
FIG. 9 is a side view of a portion of the patient support apparatus.

Similar references are used in different figures to denote similar components.

DETAILED DESCRIPTION OF THE INVENTION

Referring to FIGS. 1 to 12, a nuclear camera 5 is supported and positioned relative to a patient by a support structure 10. Nuclear cameras are heavy, usually weighing approximately three to four thousand pounds. Thus, the support structure 10 should be strong and stable in order to be able to position the camera 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. In the illustrated embodiment, the frame 35 is approximately five feet wide, five feet high, and two feet deep (e.g. approximately 1.5 m wide, 1.5 m high and 0.6 m deep). The frame 35 also includes eight triangular corner braces 40 welded to the front square section 37, that is, each corner of the front square 37 has two corner braces 40, one towards the front of the front square section 37, and one towards the rear of the front square section 37. In the illustrated embodiment, the corner braces 40 are in the shape of equilateral right angle triangles.

Attached to the underside of the face 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be leveled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. In the illustrated embodiment, the annular support 20 has an outside diameter of about fifty two inches (e.g., about 1.3 m). The annular support 20 is supported by upper rollers 80 and lower rollers 85 which are mounted on the base 15. The upper rollers 80 and lower rollers 85 roll on the outer surface 65, thus enabling the annular support 20 to rotate relative to the base 15 in the plane defined by the annular support 20 (e.g., alternatively referred to as a first plane). Each of the upper rollers 80 and lower rollers 85 are mounted onto a pair of corner braces 40 by way of axles with deep groove bearings. The bearings should be low friction and be able to withstand heavy loads.

The axles of the upper rollers 80 are radially adjustable relative to the annular support 20, so that the normal force exerted by the upper rollers 80 on the outer surface 65 is adjustable. The curved surfaces of the upper rollers 80 and lower rollers 85 (i.e. the surfaces that contact the outer surface 65) should be tough so as to be able to withstand the pressures exerted by the annular support 20, and should have a fairly high coefficient of friction so as to roll consistently relative to the annular support 20.

Attached to each pair of corner braces 40 is a stabilizing arm 90 oriented perpendicularly to the plane of the annular support 20. A pair of small stabilizing rollers 95 are mounted onto each stabilizing arm 90. Each pair of stabilizing rollers 95 is positioned such that one stabilizing roller 95 on the front surface 70, and the other stabilizing roller 95 rolls on the rear surface 75. The stabilizing rollers 95 maintain the annular support 20 in the vertical plane.

The elongate support 25 includes a pair of support arms 100, each of which extends through an aperture in the annular support 20. The nuclear camera 5 is rotatably attached to one end of the pair of support arms 100, such that the nuclear camera 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counter weight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counter weight member 110. Each counter weight link 121 is pivotally attached at its other end to a counter weight bracket 122 which is rigidly attached to the annular support 20. The counter weight links 121 are attached to the counterweight members 110 and counter weight brackets 122 using bolts and tapered roller bearings. Each counter weight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera 5, relative to the annular support 20. A pair of brackets 125 is rigidly attached to the annular support 20. A pair of rigid links 130 is pivotally attached at support arm pivot points 135 to the support arms 1100. The pair of links 130 is also pivotally attached at bracket pivot points 140 to the brackets 125. At the support and pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera 5. Each straight end 160 includes a pair of spaced apart cam followers or guides 165 slidable within the corresponding track 145. Thus, movement of the scintillation camera 5 relative to the annular support 20 (i.e. we are not concerned, at this point, with rotational movement of the scintillation camera 5 relative to the elongate support 25) is linear and parallel to the plane of the annular support 20. Note that if the camera ends 155 were pivotally attached to the support arms 100 between the nuclear camera 5 and the annular support 20, the movement of the nuclear camera 5 relative to the annular support 20 would not be linear.

Movement of the scintillation camera 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 of the illustrated embodiment is designed to operate with an apparatus for supporting and positioning a patient, such apparatus including a detached patient support 205, an engaged patient support 210, and a cylinder 245.

The detached patient support 205 includes rigid patient frame 215 supported by four casters 220. Mounted near the top of the patient frame 215 are first support wheels 225 for supporting a stretcher 227 upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera 5 and support structure 10 therefor, and for supporting and positioning a patient relative to the base 15 during operation of the scintillation camera 5 and support structure 10. To ensure that the detached patient support 205 remains stationary during operation of the scintillation camera 5, four stabilizers 233 can be lowered. Thus lowered, the stabilizers 233 ensure that the detached patient support remains stationary relative to the floor.

The engaged patient support 210 includes second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 245 is rigidly mounted to the annular support 20. The cylinder 245 is aligned with the orifice 60 of the annular support 20 such that the cylinder is coaxial with the annular support 20. The cylinder 245 includes a smooth inner surface 246 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 250. The stabilizer 250 includes outside wheels 255 to maintain the engaged patient support 210 horizontal, that is, to stop the engaged patient support from tipping relative to the cylinder 245. The outside wheels 255 roll on the outside surface 243 of the cylinder 245. The stabilizer 250 also includes end wheels 256 to prevent the engaged patient support 210 from moving in a direction parallel to the axis of the cylinder 245. The end wheels 256 roll on the ends 244 of the cylinder 245.

Figure 10:
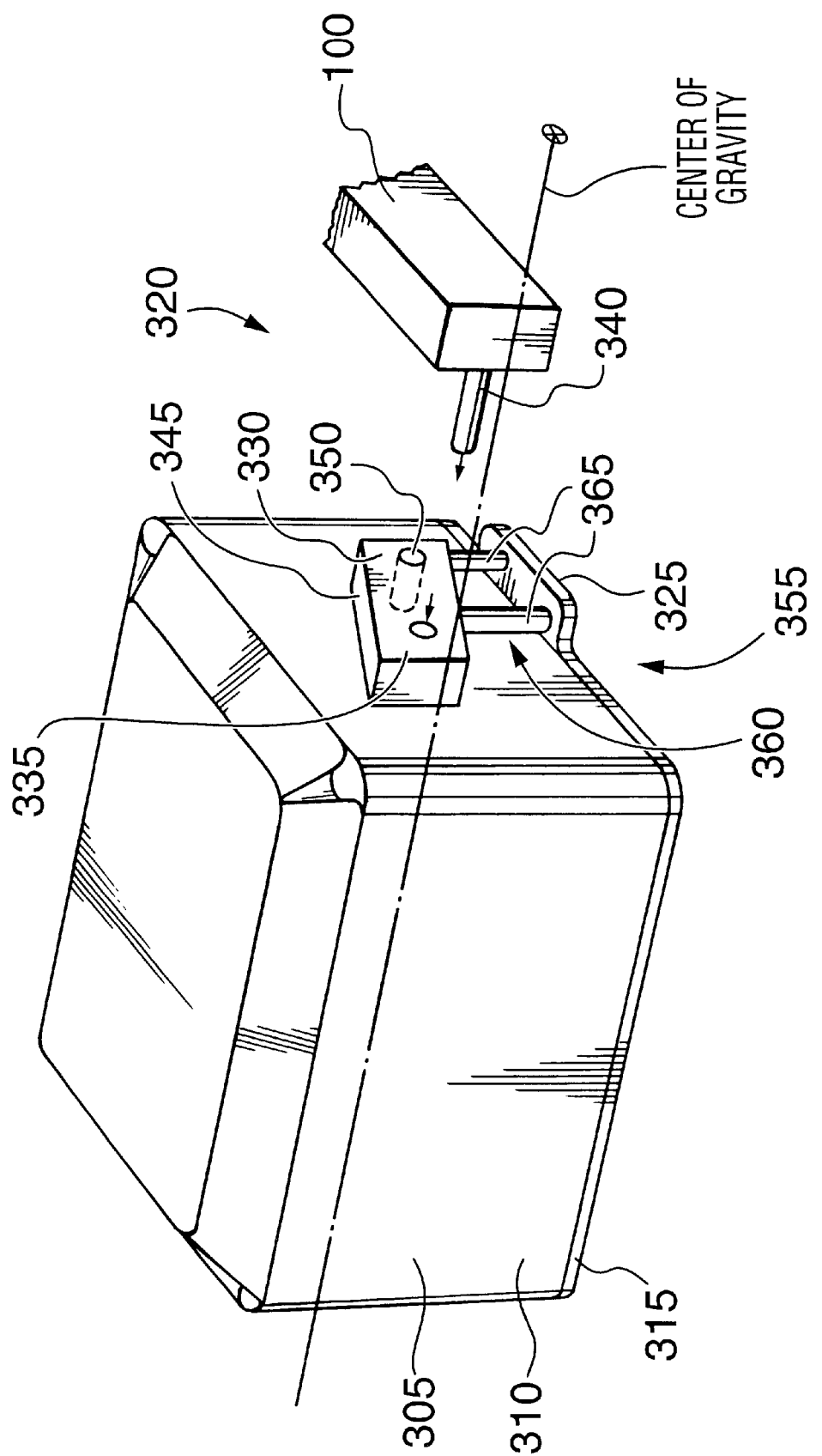
FIG. 10 is a perspective view of the positioner.
Figure 11:
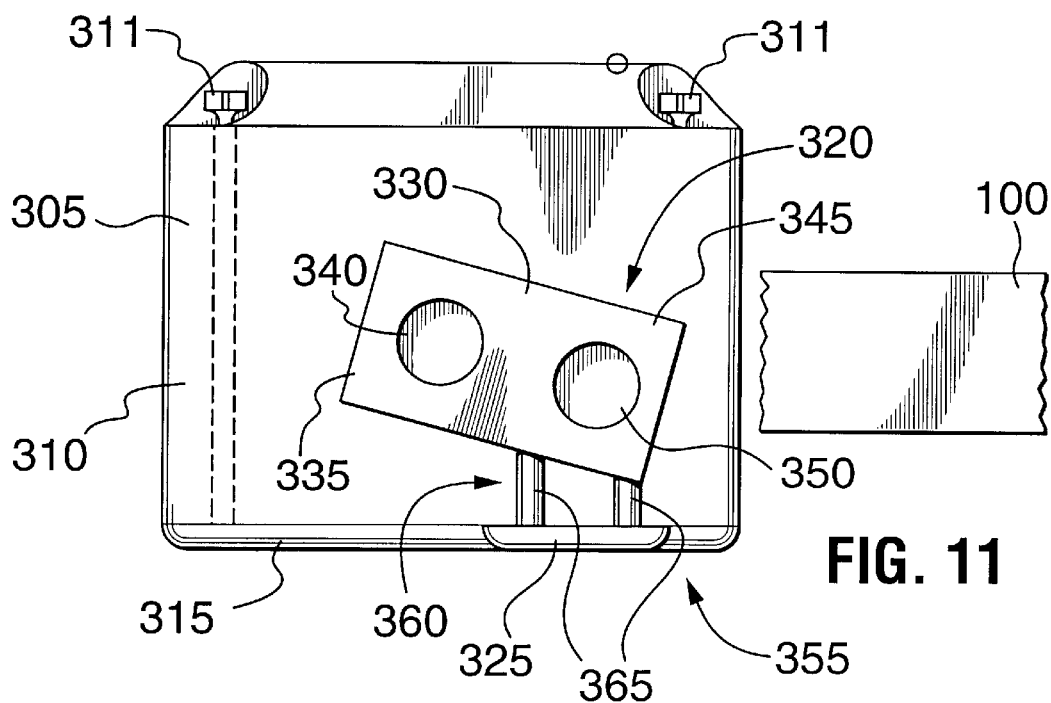
FIG. 11 is a side elevation view of the positioner.
Figure 12:
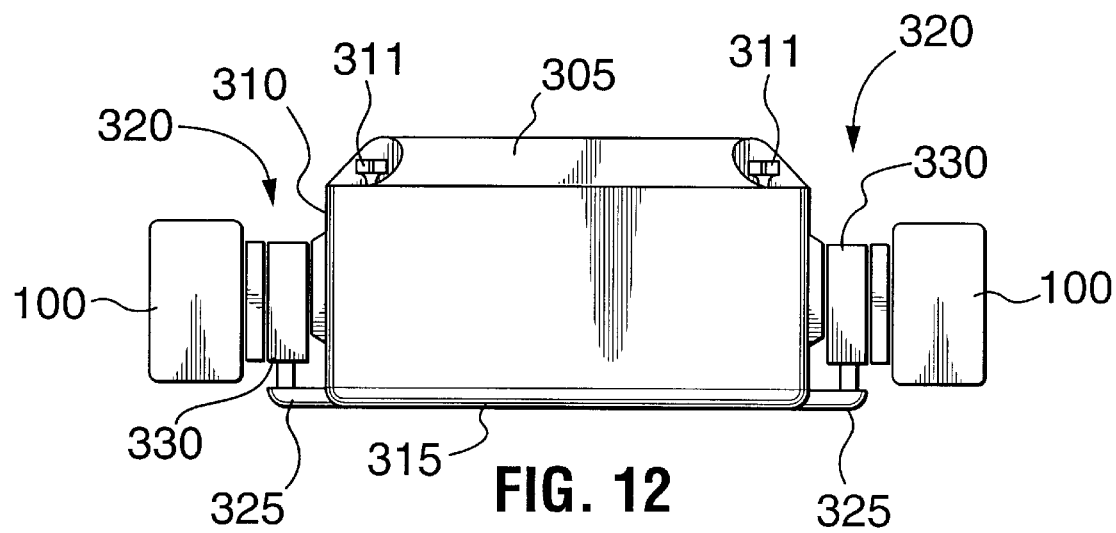
FIG. 12 is a front elevation view of the positioner.
Figure 13:
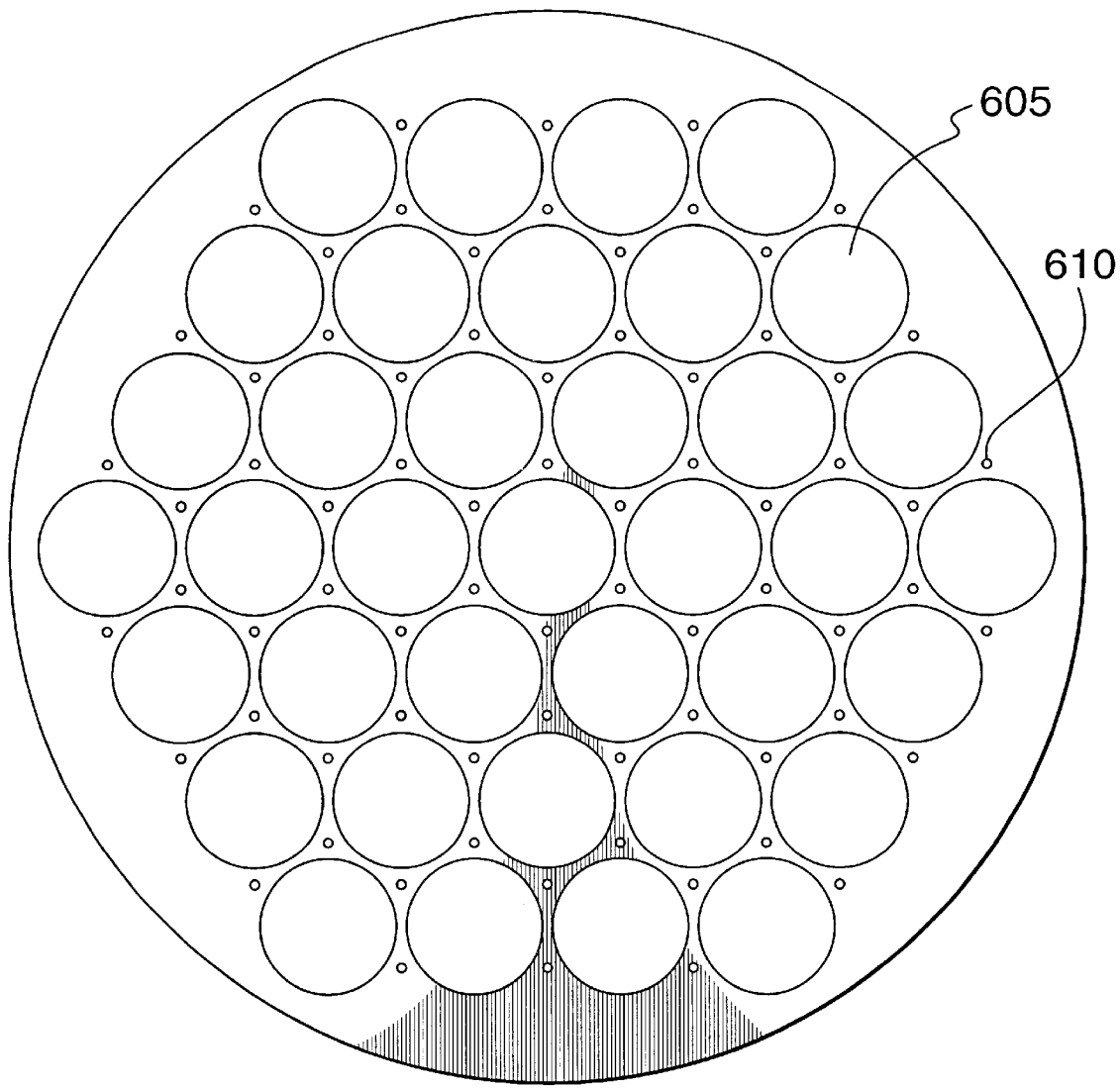
FIG. 13 is a plan view of an array of photomultiplier tubes and light sources in accordance with the present invention.

FIGS. 10, 11, and 12 illustrate a preferred embodiment of the present invention. A detector head 305 of the nuclear camera 5 is supported between the two support arms 100 by a positioner 320. The detector head 305 is supported between the two support arms 100 by a positioner 320. The detector head 305 includes a casing 310 in which is contained a scintillation crystal and photomultiplier tubes. Attached to the underside of the casing 310 is a collimator plate 315. The collimator plate 315 is made of lead perforated by narrow channels, and includes a collimator support 325 extending from the two edges of the collimator plate adjacent the support arms 100. The collimator plate 315 is attached to the casing 310 by way of bolts 311. By removing the bolts 311, the collimator 315 can be removed from the casing 31 arid replaced by another collimator plate 315. A particular design and weight of collimator is selected depending on the isotope being used or the type of study being conducted. Thus, the collimator plate 315 must be changed from time to time. Since the collimator plates 315 vary considerably in weight from one to another, the location of the center of gravity of the detector head 305 is dependent upon the weight of the collimator plate 315 attached to the casing 310. Since the angle of the detector head 305 relative to the patient must be adjusted by an operator of the nuclear camera 5, the detector head 305 must be rotatable relative to the arms 100. If the center of gravity of the detector head 305 is positioned approximately on the axis of rotation of the detector head relative to the support arms 100, then the detector head 305 will be balanced, and the angle of the detector head 305 relative to the support arms 100 will be adjustable by hand. However, changing the collimator plates moves the center of gravity of the detector head. Since collimator plates 315 are so heavy it becomes inconvenient or impossible to adjust the angle of the detector head 305 by hand. The positioner 320 enables the operator to adjust the position of the center of gravity of the detector head 305 to be approximately aligned with the point of rotation of the detector head 305, which passes through support arms 100.

The positioner 310 attaches the detector head 305 to the support arms 100 and includes a pair of rigid elongate detector head links 330 for aligning the centre of gravity of the detector head 305 relative to the support arms 100. Each detector head link 330 is rotatable relative to the support arms 310 in a plane substantially parallel to its adjacent support arm 310. Each detector head link 330 includes an arm end 335 rotatably attached to the adjacent support arm 100 by way of an arm axle 340. Each detector head link 330 also includes a head end 345 rotatably attached to the detector head 305 by way of a head axle 350.

The positioner 310 also includes a pair of locks 355 for selectively preventing rotation of the detector head 305 relative to the detector head links 330. Each lock 355 includes the collimator support 325 extending from the detector head 305 from the collimator plate 315. Each lock 355 also includes a block 360 for supporting the detector head link 330 on the collimator support 325. Each block 360 includes a pair of pins 365 located either side of the head axle 350.

Referring generally to FIGS. 13 to 16, there is shown an array of photomultiplier tubes 605 located in the detector head of a scintillation camera. Surrounding each photomultiplier tube are six light emitting diodes 610. In the present invention, there is, advantageously, more than one light emitting diode per photomultiplier tube.

The present invention allows all photomultiplier tubes to be calibrated efficiently and accurately. All light emitting diodes are pulsed simultaneously. The outputs of the photomultiplier tubes are then measured or read. The sum of all the photomultiplier tube outputs is then summed. The sum of all the photomultiplier tube outputs is then compared with an expected value, such as the sum of previously measured outputs of the photomultiplier tubes.

If the sum of the outputs of all the photomultiplier tubes is not within the tolerance, then it is likely that one or more of the light emitting diodes is malfunctioning and is in need of repair of replacement. If this is so, then the light emitting diodes are repaired or replaced and all light emitting diodes are again pulsed simultaneously, the outputs of the photomultiplier tubes are measured and then summed. Note that it may be necessary to determine whether it is in fact the light emitting diodes that are malfunctioning or the photomultiplier tubes that are malfunctioning or in need of adjustment. Such techniques are known in the art, and may involve the pulsing of individual light emitting diodes and the measurement and comparison of adjacent photomultiplier tubes.

Note that even if the sum of the outputs of all the photomultiplier tubes is not compared to an expected value in order to confirm the integrity of the light emitting diodes, the relevant embodiment includes enough light emitting diodes that the malfunctioning of one or a few light emitting diodes will not render the following steps ineffective in achieving an acceptable calibration of the photomultiplier tubes. In effect, by pulsing a large number of light emitting diodes, one achieves consistent illumination. Also, other methods may be employed to maintain the integrity of the light emitting diodes.

Once the sum of the outputs of all the photomultiplier tubes is, within the given tolerance, equal to the expected value of such sum, then the output of each photomultiplier tube is compared to its expected value, such as the value of a previously measured output of the photomultiplier tube measured after all light emitting diodes were pulsed.

If the output of a specific photomultiplier tube is, within a certain tolerance, equal to the expected value, then the photomultiplier tube is deemed to need no further calibration.

If the output of a specific photomultiplier tube is not within the tolerance, then the photomultiplier tube should be calibrated.

Optionally, a further comparison may be made. The output of each photomultiplier tube can be compared to the sum of the outputs of the photomultiplier tubes, divided by the number of photomultiplier tubes. Following such a comparison, a photomultiplier tube may be adjusted with reference to such comparison, or with reference both to such comparison and the previous comparison of the output of the photomultiplier tube to its expected value.

Once the photomultiplier tubes have been calibrated, the above process may be repeated if desired, beginning with the step of pulsing all light emitting diodes.

Figure 14:
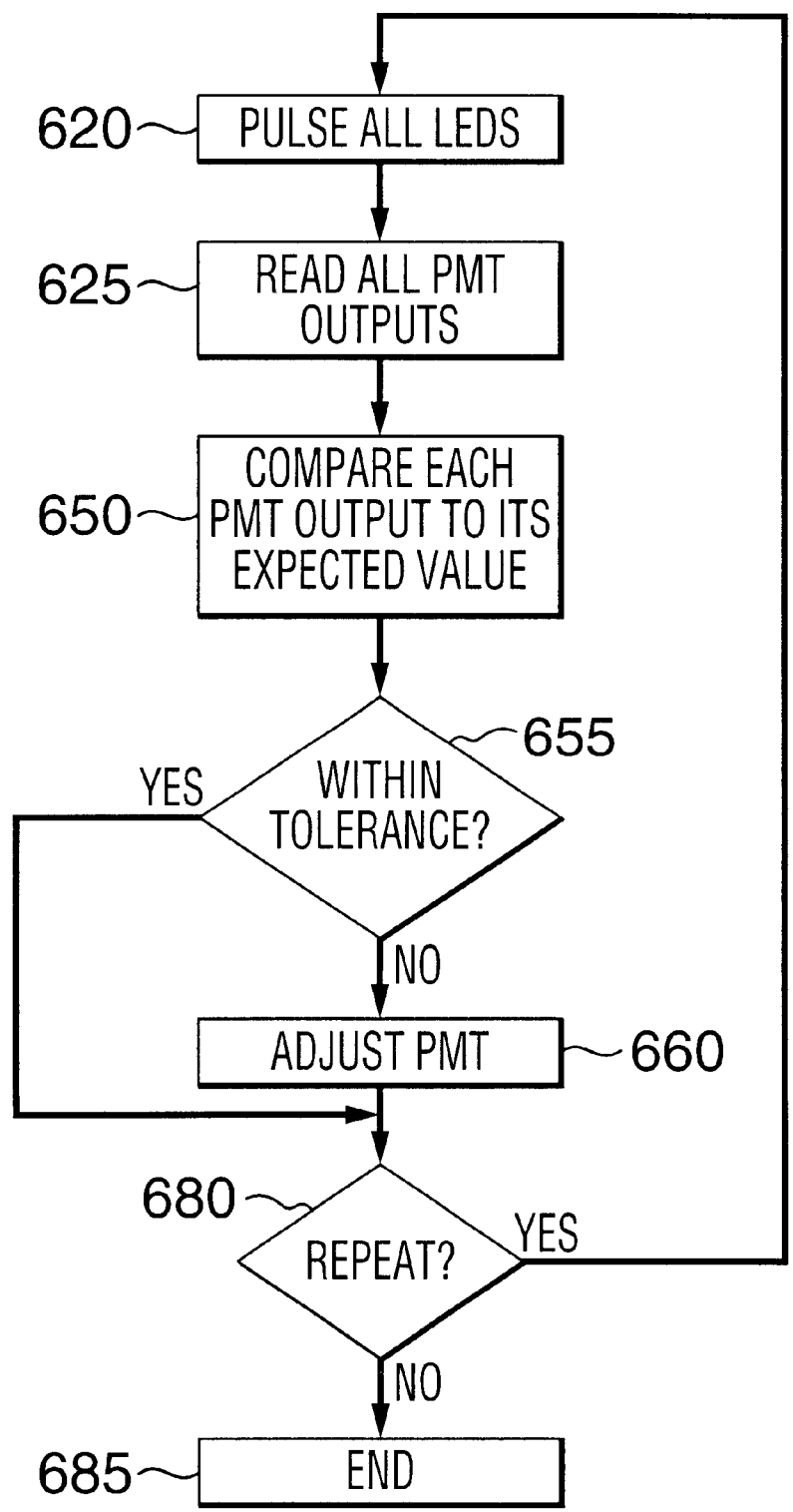
FIG. 14 is a flowchart of a first embodiment of the invention.

Referring specifically to FIG. 14, there is illustrated an embodiment of the method of the present invention. At step 620 Pulse All LEDs, or light emitting diodes, all light emitting diodes are pulsed simultaneously. At step 625 Read All PMT Outputs, or photomultiplier tube outputs, the output generated from each individual photomultiplier tube is read. At step 650 Compare Each PMT Output To Its Expected Value, the output of each individual photomultiplier tube is compared to an expected value for that particular photomultiplier tube, that is, a value that would be expected if the photomultiplier tube needed no calibration. At step 655 Within Tolerance, it is determined for each photomultiplier tube whether or not calibration is necessary, that is, whether the output of each photomultiplier tube deviates unacceptably from its expected value. At step 660, each photomultiplier tube in need of calibration is calibrated, that is, only those photomultiplier tubes whose outputs were not within the relevant tolerance values. At step 680 Repeat?, the above method is repeated if desired. Alternatively, at step 685 End, the above method is terminated.

Figure 15:
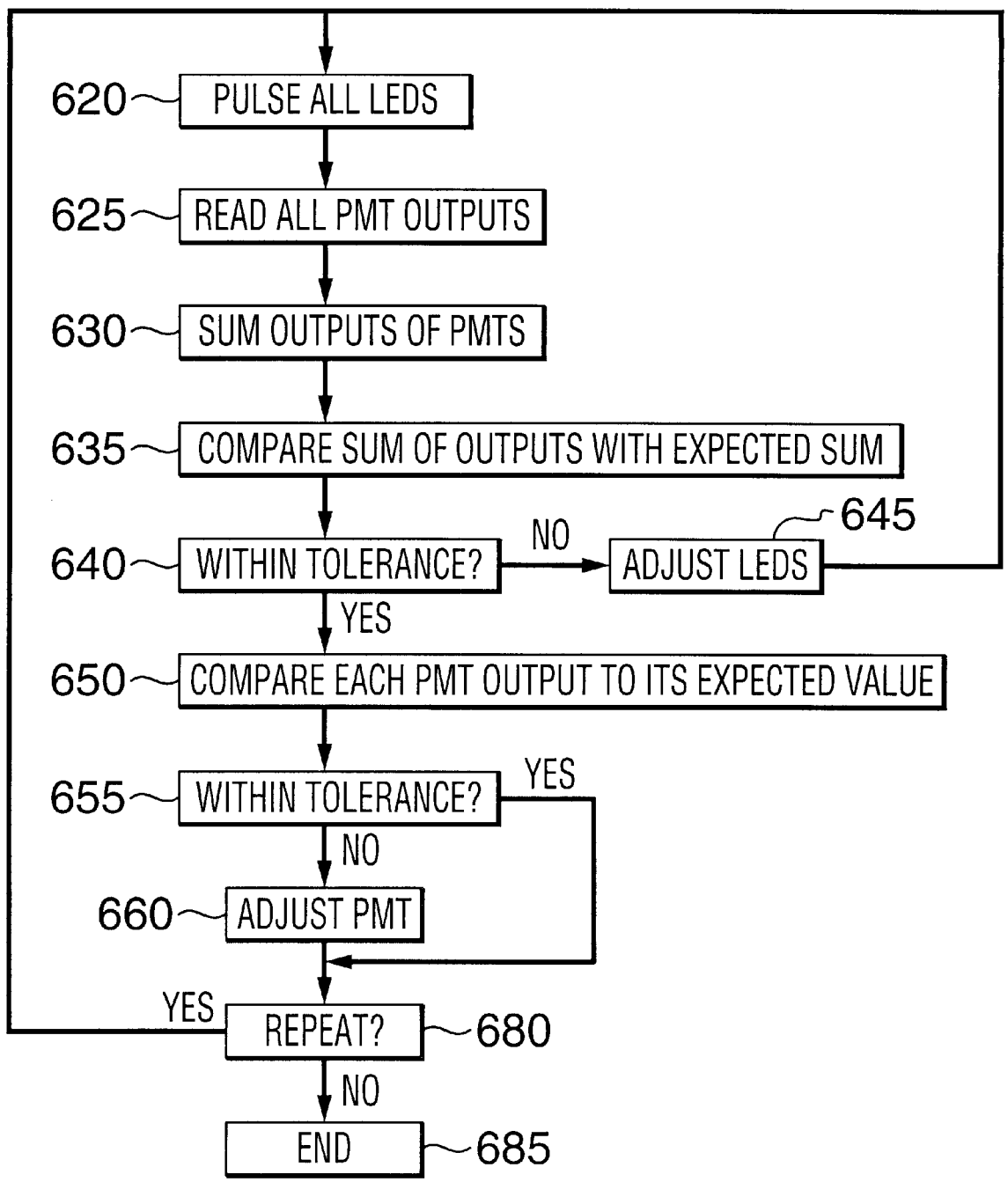
FIG. 15 is a flowchart of the second embodiment of the invention.

Referring specifically to FIG. 15, there is illustrated an embodiment of the method of the present invention. At step 620 Pulse All LEDs, or light emitting diodes, all light emitting diodes are pulsed simultaneously. At step 625 Read All PMT Outputs, or photomultiplier tube outputs, the output generated from each individual photomultiplier tube is read. At step 630 Sum Outputs Of PMTs, the outputs of each individual photomultiplier tube are added together. At step 635 Compare Sum Of Outputs with Expected Sum, the sum of the outputs of the photomultiplier tubes is compared with a value that it is expected to be if all light emitting diodes and photomultiplier tubes are functioning properly. At step 640 Within Tolerance?, a determination is made as to whether the sum of the outputs of the photomultiplier tubes is close enough to the value it is expected to be if all light emitting diodes and photomultiplier tubes are functioning properly. At step 645 Adjust LEDs, the light emitting diodes are adjusted, repaired or replaced, if necessary, if the sum of the outputs of the photomultiplier tubes is not within an acceptable tolerance. At step 650 Compare Each PMT Output To Its Expected Value, the output of each individual photomultiplier tube is compared to an expected value for that particular photomultiplier tube, that is, a value that would be expected if the photomultiplier tube needed no calibration. At step 655 Within Tolerance, it is determined for each photomultiplier tube whether or not calibration is necessary, that is, whether the output of each photomultiplier tube deviates unacceptably from its expected value. At step 660, each photomultiplier tube in need of calibration is calibrated, that is, only those photomultiplier tubes whose outputs were not within the relevant tolerance values. At step 680 Repeat?, the above method is repeated if desired. Alternatively, at step 685 End, the above method is terminated.

Figure 16:
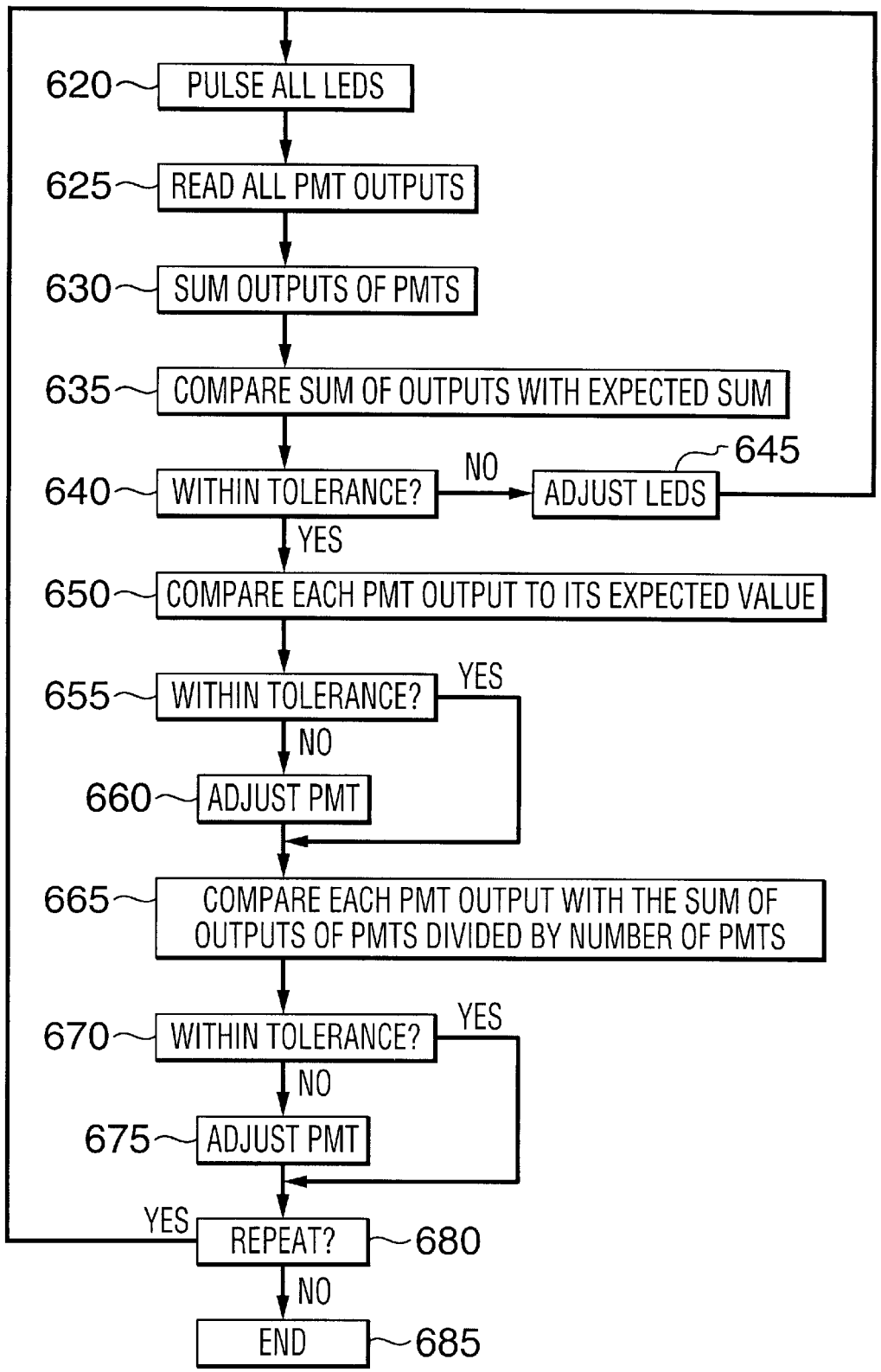
FIG. 16 is a flowchart of the third embodiment of the invention.

Referring specifically to FIG. 16, there is illustrated an embodiment of the method of the present invention. At step

620 Pulse All LEDs, or light emitting diodes, all light emitting diodes are pulsed simultaneously. At step 625 Read All PMT Outputs, or photomultiplier tube outputs, the output generated from each individual photomultiplier tube is read. At step 630 Sum Outputs Of PMTs, the outputs of each individual photomultiplier tube are added together. At step 635 Compare Sum Of Outputs with Expected Sum, the sum of the outputs of the photomultiplier tubes is compared with a value that it is expected to be if all light emitting diodes and photomultiplier tubes are finctioning properly. At step 640 Within Tolerance?, a determination is made as to whether the sum of the outputs of the photomultiplier tubes is close enough to the value it is expected to be if all light emitting diodes and photomultiplier tubes are functioning properly. At step 645 Adjust LEDs, the light emitting diodes are adjusted, repaired or replaced, if necessary, if the sum of the outputs of the photomultiplier tubes is not within an acceptable tolerance. At step 650 Compare Each PMT Output To Its Expected Value, the output of each individual photomultiplier tube is compared to an expected value for that particular photomultiplier tube, that is, a value that would be expected if the photomultiplier tube needed no calibration. At step 655 Within Tolerance, it is determined for each photomultiplier tube whether or not calibration is necessary, that is, whether the output of each photomultiplier tube deviates unacceptably from its expected value. At step 660, each photomultiplier tube in need of calibration is calibrated, that is, only those photomultiplier tubes whose outputs were not within the relevant tolerance values. At step 665 Compare Each PMT Output With The Sum Of Outputs Of PMTs Divided By Number Of PMTs, the sum of the outputs is divided by the number of photomultiplier tubes, and the output of each photomultiplier tube is compared to such value. At step 670 Within Tolerance, it is determined for each photomultiplier tube whether or not calibration is necessary, that is, whether the output of each photomultiplier tube deviates unacceptably from the average value of the photomultiplier tube outputs. At step 675, each photomultiplier tube in need of calibration is calibrated, that is, only those photomultiplier tubes whose outputs were not within the relevant tolerance values. At step 680 Repeat?, the above method is repeated if desired. Alternatively, at step 685 End, the above method is terminated.

Numerous modifications, variations and adaptations may be made to the particular embodiments of the invention described above without departing from the scope of the invention, which is defined in the claims.

I claim:

1. A method for calibrating photomultiplier tubes in a scintillation camera having a plurality of light sources, comprising the steps of:
    (a) pulsing all light sources simultaneously;
    (b) reading the output of each photomultiplier tube;
    (c) summing the outputs of the photomultiplier tubes;
    (d) comparing the sum of the outputs of the photomultiplier tubes with an expected sum;
    (e) determining whether the sum of the outputs of the photomultiplieir tubes is within a first specified tolerance;
    (f) adjusting the light sources if necessary, if the sum of the outputs of the photomultiplier tubes is not within the first specified tolerance;
    (g) repeating the steps (a) to (f) until the sum of the outputs of the photomultiplier is within the first specified tolerance;
    (h) comparing the output of each photomultiplier tube with an expected value;
    (i) determining whether the output of each photomultiplier tube is within a second specified tolerance; and
    (j) adjusting each photomultiplier tube if the output of the photomultiplier tube is not within the second specified tolerance.

2. A method for calibrating photomultiplier tubes in a scintillation camera having a plurality of light sources, comprising the steps of:
    (a) pulsing all light sources simultaneously;
    (b) reading the output of each photomultiplier tube;
    (c) summing the outputs of the photomultiplier tubes;
    (d) comparing the sum of the outputs of each of the photomultiplier tubes with an expected value;
    (e) determining whether the sum of the outputs of each of the photomultiplier tubes is within a first specified tolerance;
    (f) adjusting the light sources if necessary, if the sum of the outputs of the photomultiplier tubes is not within the first specified tolerance;
    (g) repeating steps (a) to (f) until the sum of the outputs of the photomultiplier tubes is within the first specified tolerance;
    (h) comparing the output of each of the photomultiplier tubes with an expected value;
    (i) determining whether the output of each of the photomuluiplier tubes is within a second specified tolerance;
    (j) adjusting each of the photomultiplier tubes if the output of each photomultiplier tube is not within the second specified tolerance;
    (k) comparing the output of each photomultiplier tube with the sum of the outputs of the photomultiplier tubes divided by the number of photomultiplier tubes;
    (l) determining whether the output of each photomultiplier tube is within a third specified tolerance; and
    (m) adjusting each photomultiplier tube if the photomultiplier tube is not within the third specified tolerance.

3. An apparatus for calibrating a plurality of photomultiplier tubes in a scintillation camera having a plurality of light sources, comprising:
    means for pulsing all light sources simultaneously;
    means for reading the output of each photomultiplier tube;
    means for summing the outputs of the photomultiplier tubes;
    means for comparing the sum of the outputs of the photomultiplier tubes with an expected sum;
    means for determining whether the sum of the outputs of the photomultiplier tubes is within a first specified tolerance;
    means for adjusting the light sources if necessary, if the sum of the outputs of the photomultiplier tubes is not within the first specified tolerance;
    means for comparing the output of each photomultiplier tube with an expected value;
    means for determining whether the output of each photomultiplier tube is within a second specified tolerance; and
    means for adjusting each photomultiplier tube if the output of the photomultiplier tube is not within the second specified tolerance.

4. An apparatus as defined in claim 3, wherein each photomultiplier tube is adjacent to six light sources.

5. An apparatus as defined in claim 4, wherein the light sources are light emitting diodes.

6. An apparatus for calibrating a plurality of photomultiplier tubes in a scintillation camera having a plurality of light sources, comprising:

means for pulsing all light sources simultaneously;

means for reading the output of each photomultiplier tube;

means for summing the outputs of the photomultiplier tubes;

means for comparing the sum of the outputs of the photomultiplier tubes with an expected sum;

means for determining whether the sum of the outputs of the photomultiplier tubes is within a first specified tolerance;

means for adjusting the light sources if necessary, if the sum of the outputs of the photomultipler tubes is not within the first specified tolerance;

means for comparing the output of each photomultiplier tube with an expected value;

means for determining whether the output of each photomultiplier tube is within a second specified tolerance;

means for adjusting each photomultiplier tube if the output of the photomultiplier tube is not within the second specified tolerance;

means for adjusting each photomultiplier tube if the output of the photomultiplier tube is not within the second specified tolerance;

means for comparing the output of each photomultiplier tube with the sum of the outputs of the photomultiplier tubes divided by the number of photomultiplier tubes;

means for determining whether the output of each photomultiplier tube is within a third specified tolerance; and means for adjusting each photomultiplier tube if the photomultiplier tube is not within the third specified tolerance.

7. An apparatus as defined in claim 5, wherein each photomultiplier tube is adjacent to six light sources.

8. An apparatus as defined in claim 7, wherein the light sources are light emitting diodes.

* * * * *